United States Patent [19]

Kessler

[11] 4,257,886

[45] Mar. 24, 1981

[54] APPARATUS FOR THE SEPARATION OF BLOOD COMPONENTS

[75] Inventor: Stephen B. Kessler, North Bergen, N.J.

[73] Assignee: Becton, Dickinson and Company, East Rutherford, N.J.

[21] Appl. No.: 4,450

[22] Filed: Jan. 18, 1979

[51] Int. Cl.³ .................... B01D 12/00; B01D 43/00
[52] U.S. Cl. ................... 210/516; 206/524.3; 210/927
[58] Field of Search .......... 210/31 C, 83, 513–516, 210/518, DIG. 23, DIG. 24; 233/1 R, 1 A, 26; 128/272, 2 G, DIG. 5, DIG. 21; 23/258.5 R, 259, 292; 206/524.3; 427/2, 230; 106/2; 215/1 C, DIG. 3, DIG. 6

[56] References Cited

U.S. PATENT DOCUMENTS

| | | | |
|---|---|---|---|
| 2,504,482 | 4/1950 | Goldman | 206/524.3 |
| 3,852,194 | 12/1972 | Zine | 210/DIG. 23 |
| 3,958,045 | 5/1976 | Coleman | 427/230 |
| 3,997,442 | 12/1976 | Gigliello et al. | 210/DIG. 23 |
| 4,043,905 | 8/1977 | Novotny et al. | 210/31 C |

Primary Examiner—Frank Sever
Attorney, Agent, or Firm—Burns, Doane, Swecker & Mathis

[57] ABSTRACT

An improved assembly for use in the centrifugal separation of serum or plasma from blood is disclosed. A tubular glass container has therein a body of gel-like material having a yield stress value such as to permit it to flow and form a transverse barrier between the separated phases of blood upon centrifugation. This container is provided with an hydrophobic inner surface portion adjacent to said barrier to enhance the adhesion of the barrier material to the container wall and inhibit leakage across the barrier of the separated blood components.

9 Claims, 3 Drawing Figures

U.S. Patent    Mar. 24, 1981    4,257,886
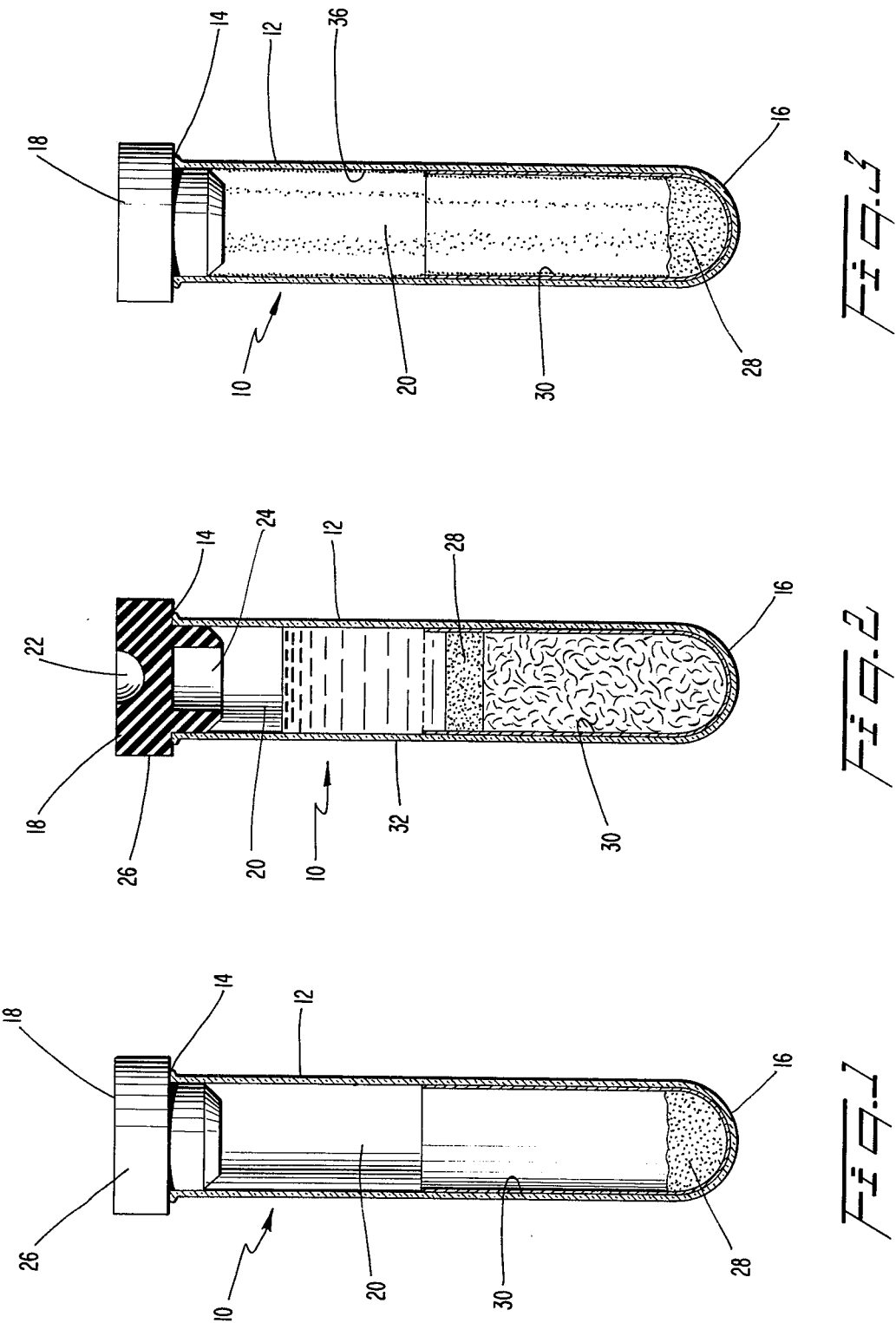

APPARATUS FOR THE SEPARATION OF BLOOD COMPONENTS

BACKGROUND OF THE INVENTION

This invention relates to the centrifugal separation of the heavier and lighter phases of whole blood and is concerned particularly with a blood container assembly suitable for the centrifugal separation operation and having an improved capacity for preventing migration and remixing of the separated blood phases.

A type of centrifugal blood separation assembly known in the art employs a glass tubular container having therein a body of gel-like barrier material which, upon centrifugation, will form a transverse barrier between the lighter and heavier phases of whole blood, e.g., the lighter liquid and heavier, substantially cellular phases. For example, U.S. Pat. No. 3,780,935 discloses such a system in which barrier material is injected into a blood collection container during centrifugation. For somewhat similar disclosures, see also U.S. Pat. Nos. 3,976,579 and 3,986,962. U.S. Pat. 3,852,194 deals with apparatus which differs from that disclosed in U.S. Pat. No. 3,780,935 in that the barrier material is loosely disposed within the bottom of a tubular collection chamber.

In U.S. Pat. No. 3,920,549, gel-like barrier material is loosely disposed within a tubular blood collection chamber and an energizer device is used to influence the flow of the material during centrifugation, causing it to flow along the inner surfaces of the collection chamber. It is further disclosed that the inner surface of the collection chamber may be coated with a lubricant, such as a polyethylene oxide polymer, to prevent adhesion of blood thereto. Lessened adhesion of the blood to the inner surface reduces the likelihood of rupturing of red blood cells due to collision of the barrier material with red blood cells which have adhered to the inner surface.

Although the use of a gel-like material to create a barrier between the centrifugally separated phases of whole blood has proved to be a beneficial approach, certain problems still exist. One such problem is leakage past the barrier of one blood phase into the other. With the equipment available prior to the present invention, such leakage was observed after extended periods of time and, particularly, in instances where the collection chamber was placed on its side.

SUMMARY OF THE INVENTION

It is therefore an object of this invention to provide an improved assembly for the separation of the different phases of blood wherein a gel-like material is used to form a more effective barrier beetweeen the separated phases.

The improved separation tube assembly of this invention comprises a blood container having therein a body of gel-like material having a yield stress value such as to permit it to flow upon centrifugation and form a barrier between the separated phases of the blood, with the portion of the inner surface of the container adjacent to the barrier being hydrophobic in nature. With this arrangement, the barrier material can adhere to a hydrophobic container surface to prevent the separated blood phases from communicating with each other subsequent to the centrifugation operation.

In a preferred embodiment, the blood separation container is a glass tube having a closed end toward which the heavier blood components will moe during centrifugation and a hydrophobic coating is provided on the interior surface of that portion of the tube which will be contacted by the barrier material and the heavier blood phase. The remaining interior surface of the glass tube is not coated with the hydrophobic material and it remains hydrophilic so as to minimize the likelihood that blood clots will adhere thereto and be inhibited from moving toward the closed end of the tube during centrifugation.

In another preferred embodiment, a water-soluble, clot-activating coating is employed to cover the entire inner surface of the container that will contact the blood. That is to say, the clot-activating coating covers both the hydrophobic surface at the bottom half of the container and the hydrophilic surface at the top half of the container. Such clot-activating coatings are compatible with other components of this invention, and the presence of such a coating counteracts whatever tendency toward deceleration of the clotting action might be associated with the presence of the hydrophobic coating.

Thus, the invention is not only effective in the collection and centrifugal separation of the blood but also assures that the blood phases will remain separated for extended periods of time as well as when the tubes are laid on their sides. This improved performance contributes significantly to the range of testing programs in which the equipment may be used.

BRIEF DESCRIPTION OF THE DRAWINGS

FIG. 1 is a longitudinal cross-sectional view of a centrifugal separation assembly embodiment of the present invention.

FIG. 2 is a similar view illustrating this embodiment after having been filled with a multiphase liquid such as blood and centrifuged to separate the phases, with a body of barrier material having formed a transverse barrier between the separated phases.

FIG. 3 is a longitudinal cross-sectional view of a modification of the centrifugal separation assembly embodiment of FIG. 1 wherein the use of a clot-activating coating is additionally depicted.

DETAILED DESCRIPTION OF A PREFERRED EMBODIMENT

The serum or plasma separation assembly 10 of the Figures includes a glass tubular container 12 having an open end 14 and a closed end 16. The open end 14 of the assembly is closed with a self-sealing, elastomeric closure means 18 which hermetically seals said open end.

When the closure means 18 is in place, the assembly 10 provides a chamber 20 which may be partially air-evacuated so as to provide a partial vacuum in the chamber. This partial vacuum assists importantly in filling the container with a blood sample in the ordinary way.

The elastomeric closure means 18 is preferably provided with a recess 22 in its upper surface and a deep axial recess 24 in its lower surface. A cannula-penetrable zone 26 lies between the recess 22 and the axial recess 24.

A body of barrier material 28 is loosely disposed adjacent the closed end 16. Suitable barrier materials are gel-like in nature and chemically inert to the separated phases of blood. Such materials should have yield stress values such that they do not flow substantially in the absence of forces of the magnitude encountered during centrifugation but do flow during centrifugation to permit the material to occupy a position between separated blood phases. The barrier material will thus have a yield stress value in the range of from about 200 to about 4000, preferably from about 400 to 2500, and most preferably from about 600 to about 1000 dynes/cm$^2$.

Such gel-like barrier materials are commonly employed to form transverse layers or barriers between the separated phases of blood and are well known in the art. A typical material which may be employed in this invention is a silicone oil thickened with fumed silicon dioxide. This material is gel-like and hydrophobic in nature.

The specific gravity of the barrier material must be intermediate the specific gravities exhibited by the separated phases of blood in order to be capable of forming a transverse barrier or layer therebetween upon centrifugation. Generally the barrier material will have a specific gravity within the range of from about 1.03 to 1.09, preferably from about 1.04 to about 1.06. This range enables the material to form a transverse barrier between the heavy and light phases of blood. The disclosures of U.S. Pat. No. 3,780,935 and U.S. Pat. No. 3,852,194 are herein incorporated by reference for discussion of various materials which may be employed as the barrier material in the centrifugal separation of the different phases of blood.

While the body of barrier material is shown to be disposed adjacent the closed end 16 of the container 12, any means by which the barrier material may be placed within the container is satisfactory so long as a transverse barrier is formed between the separated fluid phases of the blood upon centrifugation of the assembly. For example, U.S. Pat. No. 3,986,962 and U.S. Pat. No. 3,976,579, each herein incorporated by reference, each disclose generally suitable alternative means.

A portion 30 of the inner wall of the chamber 20 is hydrophobic in nature. Specifically, at least the portion which is adjacent to the barrier subsequent to centrifugation is hydrophobic. Such placement of the hydrophobic surface 30 ensures that the barrier material may cooperate with and adhere to the hydrophobic surface to form a complete barrier between the separated phases of blood. As will become readily apparent from the following discussion, the hydrophobic portion 30 of the inner wall of the chamber has been depicted in a somewhat exaggerated dimension relative to the assembly 10 in order to clearly show its position along the inner surface.

Any hydrophobic, water-insoluble composition which can be applied to the inner surface of the container 12 to provide the required hydrophobic surface while also being resistent to migration is suitable for use. Liquid coatings such as silicone oil would not be suitable since they would tend to migrate along the inner surface of the container. Similarly, water-soluble coatings such as the polyethylene oxide polymer used in U.S. Pat. No. 3,920,549 are unsuitable since they would tend to be dispersed upon contact with the blood and centrifugation of the assembly.

Suitable hydrophobic coating compositions are known in the art. Exemplary hydrophobic, water-insoluble coatings may be formed from polymeric silicone compounds (e.g., organo polysiloxanes). Silicone compounds exhibit extreme water repellancy and thus are highly desirable for use as the hydrophobic coating. Preferably the coating composition comprises a silicone coating which is chemically bonded to the inner surface of the container 12 and is formed from a reactive silane compound.

A suitable polymeric silicone composition is a chlorine-substituted polysiloxane manufactured by the Pierce Chemical Company and identified by the designation "SurfaSil." Another composition which may be used to form a silicone coating on the inner surface comprises a mixture of a reactive polysiloxane and solvents and is marketed by Clay-Adams, Inc. under the designation "Siliclad."

Other types of hydrophobic, water-insoluble compositions may be employed to form the coating. Tetrafluoroethylene, marketed by E.I. DuPont Nemours & Co. under the designation of "Teflon," also produces satisfactory results when employed as the hydrophobic, water-insoluble, coating composition.

An exemplary method of providing the hydrophobic coating is as follows. A dilute solution (i.e., 5 percent) of "SurfaSil" in toluene is prepared. A syringe having a needle which is sufficiently long to reach the closed end 16 of the container 12 is filled with the dilute solution. The dilute solution within the syringe is then forced into the container 12 to a level whereby the desired portion of the inner surface of the container 12 is coated with the hydrophobic composition. After allowing a brief retention period, typically five seconds or so, the solution is withdrawn from the container 12. The solvent in the coating is allowed to evaporate and a hydrophobic coating is formed which is chemically bonded to the inner surface and will not migrate along the inner surface. The hydrophobic coating may initially exhibit acidic properties due to the presence of hydrochloric acid formed by the hydrolysis of the chlorine atoms contained within the "SurfaSil" composition. However, drying the coated container for 30 minutes at 100° C. will hasten the removal of the hydrochloric acid by evaporation and provide a neutral hydrophobic coating. Drying under ambient conditions will also provide a neutral surface but the drying time will be longer.

The disclosure of U.S. Pat. No. 2,504,482 is herein incorporated by reference for further discussion of methods for coating the inner surface of containers with thin silicone films to provide a bonded hydrophobic coating thereon. The disclosure of U.S. Pat. No. 2,832,701 is also incorporated by reference for a discussion of the use of colloidal silica in the coating of glass containers to provide a hydrophobic surface.

It is desirable to avoid the use of a container whose entire inner surface is substantially or completely hydrophobic in nature. Clotted red blood cells are hydrophobic and are preferentially attracted to a hydrophobic surface. If the entire inner surface of the container 12 exhibits hydrophobic properties, clotted red blood cells would be attracted to the entire inner surface. Such a result is disadvantageous when blood is being separated into heavier and lighter phases. The lighter liquid portion is referred to as blood serum if the blood is clotted or plasma if the blood is not clotted. Clotted red blood cells normally comprise part of the heavier portion of the separated phases (i.e. the portion remaining after separation of the blood serum), and it would be difficult to completely separate the clotted cells from a lighter phase if the clotted cells were attached to the wall of that portion of the tube to be occupied by the lighter phase.

Accordingly, it is most desirable to employ a container 12 whose inner surface is hydrophobic in only those portions which, upon centrifugation, would be adjacent to a separated heavier phase and the transverse barrier. Since hematocrit values of 40 to 60 percent are normal, the hydrophobic coating 30 will normally be located on the bottom half of the container 12 adjacent to the closed end 16. More generally, the lower 40 to 60 percent of the length of the inner surface of the container 12 will normally need to be coated with hydrophobic material in order to provide an adjacent hydrophobic surface for the barrier material and the heavier portion of the blood.

Since glass exhibits hydrophilic properties, the portions of the inner surface of a glass container which are not hydrophobic will be hydrophilic. That is, if substantially the half of the inner surface of the container adjacent the closed end 16 is hydrophobic, then substantially the upper half of the inner surface adjacent the open end 14 will be hydrophilic.

If it is desired to separate plasma as the lighter phase 32, the chamber 20 may be precharged with an anticoagulant so that the whole blood admixes with the anticoagulant upon entering the chamber.

If serum is desired, however, the blood may be allowed to stand within the chamber 20 for a period of time so that clotting of the red blood cells may occur. The time taken to form a blood clot in collected blood is dependent to some extent upon the rate of conversion of prothrombin to thrombin and of fibrinogen to fibrin. One of the factors which increases the rate of clot formation is exposure of the blood to "siliceous" materials such as glass, silica, kaolin, bentonite, siliceous aluminum hydrate, and diatomaceous earth or kieselguhr. See, for example, Soulier et al, British Journal of Haemetology, Vol. 6, pages 88 through 101 (1960).

Clotting may thus be aided by the application of a water-soluble, clot-activating coating 36 to the inner surface of the container 12 prior to the introduction of blood as depicted in FIG. 3. The clot-activating coating may be added after the hydrophobic coating 30 has been applied. The clot-activating coating may contain any of the well-known clot-forming materials discussed above. Upon contact with the blood, the clot-activating coating dissolves, whereupon the clot-forming materials therein are released into the blood and initiate the clotting process. The blood is allowed to sit until sufficient clotting of the red cells has taken place.

The coating which contains the clot-forming materials must be water-soluble and inert with respect to the blood and blood testing reagents. The term inert as used herein means that the coating material will not enter into or otherwise adversely affect the desired separation of the light, liquid phase of the blood from the heavy, substantially cellular phase, nor will it interfere with conventional diagnostic tests to be performed upon either component phase of the blood. Exemplary coating materials are water-soluble polymers such as polyvinylpyrrolidone or poly(ethylene oxide) admixed with clot-activating particles such as silica.

The clot-activating coating may be applied in a conventional manner. For example, a water-soluble polymer admixed with a clot-forming material may be added to a suitable solvent (e.g. isopropanol) to form a homogenous mixture. The inner surface of the container is then coated with the mixture, and the solvent allowed to evaporate. A water-soluble coating of the clot-activating material is thus formed.

The manner in which the invention is used now will be evident. A blood-bearing cannula is introduced through the cannula-penetrable zone 26 of the closure means 18 into the collection chamber 20. The partial vacuum within the collection chamber 20 draws the blood from the cannula into the collection chamber. When the collection chamber is filled with blood to an appropriate level, the cannula is withdrawn and the closure means 18 seals itself.

The blood is then centrifuged in a conventional manner, whereby the blood is separated into a component light phase such as plasma or serum 32 and a heavy substantially cellular phase 34 as illustrated in FIG. 2. During centrifugation of the assembly 10 the heavy portion 34 is forced toward the closed end 16 of the container 12. The centrifugation step also causes the body of gel-like barrier material 28 to be displaced to a position between the heavier phase 34 and the lighter phase 32. The material thus forms a transverse barrier or layer between the heavier and lighter phases. The barrier material adheres to the hydrophobic surface 30 and forms a complete and durable barrier between the separated phases of the blood.

Due to the improved seal formed between the barrier material and the hydrophobic inner surface of the container, the assembly 10 may be handled or transported after separation and isolation of the different phases of the blood, without fear of easily remixing the separated phases.

Although the present invention has been described in connection with separating a serum or plasma phase from blood, some of its features may be used in connection with the separation of other fluids having phases of different densities.

While the invention has been illustrated and described in connection with a preferred embodiment thereof, it is to be understood that this is illustrative rather than restrictive and that various modifications may be made without departing from the spirit of the invention or the scope of the claims.

I claim:

1. An assembly for use in the centrifugal separation of heavy and light phases from blood, said assembly comprising: a blood container having therein a body of barrier material which is chemically and physically inert to the separated phases of blood and capable of forming a transverse barrier between the heavier and lighter phases of blood upon centrifugation, the portion of the inner surface of the container which is adjacent to the transverse barrier formed by the barrier material upon centrifugation being hydrophobic so as to provide an improved seal between the container surface and the barrier due to the adherence of said barrier material to said hydrophobic portion of said inner surface to ensure against migration across the barrier of separated blood phases.

2. The assembly of claim 1 wherein the hydrophobic portion of the inner surface of the container is substantially that portion of the inner surface which is adjacent to and contacts the separated heavier phase and the transverse barrier upon centrifugation.

3. The assembly of claim 1 wherein the hydrophobic portion of the inner surface of the container comprises a coating of a hydrophobic, water-insoluble composition which will not migrate along said inner surface.

4. The assembly of claim 3 wherein the container is glass and wherein the hydrophobic coating comprises a silicone coating chemically bonded to the glass.

5. The assembly of claim 1 wherein the inner surface of the container is coated with a water-soluble, clot-activating coating.

6. An assembly for use in the centrifugal separation of heavy and light phases from blood, said assembly after centrifugation comprising:
   a. a tubular container having a glass body formed with an open end and a closed end;
   b. a closure hermetically sealing said open end;
   c. a transverse barrier between separated heavier and lighter phases of blood within the tubular container, said barrier being chemically and physically inert to the separated phases of blood; and
   d. a hydrophobic, water-insoluble coating fixed to the inner surface of the tubular container so as to prevent migration thereof along said surface, said coating being positioned adjacent said barrier such that an improved seal is provided between said separated phases of blood due to the adherence of said barrier material to said hydrophobic coating.

7. The assembly of claim 6 wherein the hydrophobic coating comprises a silicone coating chemically bonded to said glass body.

8. The assembly of claim 6 wherein said hydrophobic, water-insoluble coating also covers that portion of the inner surface of the tubular container which is adjacent to and contacts the separated heavier blood phase.

9. The assembly of claim 8 wherein the inner surface of the tubular container which is adjacent to and contacts the separated lighter blood phase is hydrophilic.

* * * * *